United States Patent
Doth et al.

[11] Patent Number: 5,925,533
[45] Date of Patent: Jul. 20, 1999

[54] TROPININ I CALIBRATOR AND METHOD OF USE THEREOF IN A SANDWICH IMMUNOASSAY

[75] Inventors: Margit Doth; Christoph Petry, both of Krefeld; Nicole Petesch, Wuppertal, all of Germany

[73] Assignee: Bayer Aktiengesellschaft, Leverkusen, Germany

[21] Appl. No.: 08/763,374

[22] Filed: Dec. 13, 1996

[30] Foreign Application Priority Data

Dec. 21, 1995 [DE] Germany .................. 195 48 028

[51] Int. Cl.$^6$ .................................. G01N 33/53
[52] U.S. Cl. .................. 435/7.94; 435/7.1; 435/967; 435/972; 436/518; 436/8; 436/15; 436/811; 436/815; 530/391.1; 530/391.5; 530/391.7; 530/391.9; 530/807
[58] Field of Search .................. 435/7.1, 7.92, 435/7.93, 7.94, 7.95, 70.21, 240.27, 965, 967, 972; 436/518, 531, 8, 811, 815, 15; 530/391.1, 391.5, 391.7, 391.9, 807

[56] References Cited

U.S. PATENT DOCUMENTS

| | | | |
|---|---|---|---|
| 4,962,188 | 10/1990 | Frankel | 530/391.7 X |
| 5,045,312 | 9/1991 | Aston | 530/391.9 X |
| 5,126,241 | 6/1992 | Schenk | 435/7.93 X |
| 5,204,449 | 4/1993 | Puri | 530/391.7 |
| 5,399,672 | 3/1995 | Jalalian et al. | 530/391.1 X |
| 5,620,686 | 4/1997 | Mason | 530/391.7 X |
| 5,639,670 | 6/1997 | Bergmann et al. | 435/7.94 X |

FOREIGN PATENT DOCUMENTS

| | | |
|---|---|---|
| 650053 | 4/1995 | European Pat. Off. . |
| 2275774 | 9/1994 | United Kingdom . |
| 94/27156 | 11/1994 | WIPO . |
| 9427156 | 11/1994 | WIPO . |

OTHER PUBLICATIONS

Williams G. "Novel Antibody Reagents: Production and Potential Trends in Biotechnology", Bd. 6, Nr. 2, Feb. 1988, pp. 36–39, 42 XP000009941.

English Abstract of EP 650,053.

S.S. Wong, *Chemistry of Protein Conjugation and Cross–Linking*, 1991, CRC Press Inc. ISBN 0–8493–5886–8, Table of Contents, only.

S. Yoshitake et al, Eur.J. Biochem., 101:395, 1979.

W.J. Vallins et al, *Molecular Cloning of Human Cardiac Troponin I Using Polymerase Chain Reaction*, FEBS 270:37–61, 1990.

Biosis No. 73032155 abstract of Oeltmann et al., "Inhibition of Mouse Spleen Cell Function by Diptheria Toxin Fragment A Coupled to Anti–Mouse THY–1.2 and by Ricin A Chain Coupled to Antimouse Immunoglobulin M," *Arch. Biochem. Biophys*, 209(2):362 (1981).

*Primary Examiner*—Carol A. Spiegel
*Attorney, Agent, or Firm*—Sprung Kramer Schaefer & Briscoe

[57] ABSTRACT

A conjugate consisting of a sequence of the analyte and an antibody against one of the antibodies used in the test can be employed, in aqueous solution and in precisely known quantity, as a stable calibrator in a sandwich immunoassay for detecting the analyte.

7 Claims, 2 Drawing Sheets

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 13 amino acids
      (B) TYPE: amino acid
      (D) TOPOLOGY: linear (xi) SEQUENCE DESCRIPTION: SEQ ID NO: 1:

Arg Ala Tyr Ala Thr Glu Pro His Ala Lys Lys Lys Ser
 1           5                 10

(2) INFORMATION FOR SEQ ID NO:2:

(i) SEQUENCE CHARACTERISTICS:
      (A) LENGTH: 20 amino acids
      (B) TYPE: amino acid
      (D) TOPOLOGY: linear (xi) SEQUENCE DESCRIPTION: SEQ ID NO: 2:

-continued

```
Thr Gly Leu Gly Phe Ala Glu Leu Gln Asp Leu Cys Arg Gln Ile
1               5                   10                  15
His Ala Arg Val Asp
                20
```

TROPININ I CALIBRATOR AND METHOD OF USE THEREOF IN A SANDWICH IMMUNOASSAY

BACKGROUND OF THE INVENTION

1. Field of the Invention

The present invention relates to a synthetic calibrator and its use in a sandwich immunoassay.

2. Description of Related Art

On account of their particularly good specificity and sensitivity, immunoassays are frequently employed for detecting proteins, for the purposes of medical diagnosis, in serum samples or urine samples. This requires, in addition to one or two specific antibodies, a calibrator, which is used as a comparison standard for quantifying the patient samples. It is desirable to be able to store the calibrators at 4° C. for periods of several weeks to months, particularly in the case of automated assays carried out in large analytical laboratories. Depending on the analyte, these demands placed on the stability of the calibrator formulation can give rise to difficulties if, for example, there is no guarantee of solubility under physiological salt and pH conditions. As an example, mention may be made in this context of troponin I and troponin T, which are only adequately stable and soluble in denaturing solutions (6 M urea, 0.01 M dithiothreitol). However, it is not possible to establish any immunoassay using this denaturing formulation, since the antibodies are damaged by this treatment.

It is known that proteins are relatively unstable in solution and that reagents containing them are frequently sold in freeze-dried form, together with a solvent of suitable composition in which the experimenter has to dissolve them prior to use. If the solutions which are obtained in this way are stored at 4° C., they can be used for several days even if daily determination indicates that the concentration of the reagent is changing to some extent. In general, therefore, it is recommended—in the case of troponin I (TnI) and troponin T (TnT) as well—that the comparison solutions which are obtained from the freeze-dried material be frozen in unit-dose form if they are to be stored for a relatively long period.

SUMMARY OF THE INVENTION

The present invention relates to a process for preparing a synthetic calibrator for use in a sandwich immunoassay. The synthetic calibrator consists of an antibody against one of the antibodies used in the assay and a sequence of the analyte.

BRIEF DESCRIPTION OF THE DRAWINGS

The invention will now be described in more detail with reference to the drawings, wherein.

DESCRIPTION OF THE PREFERRED EMBODIMENTS

Figure 1:
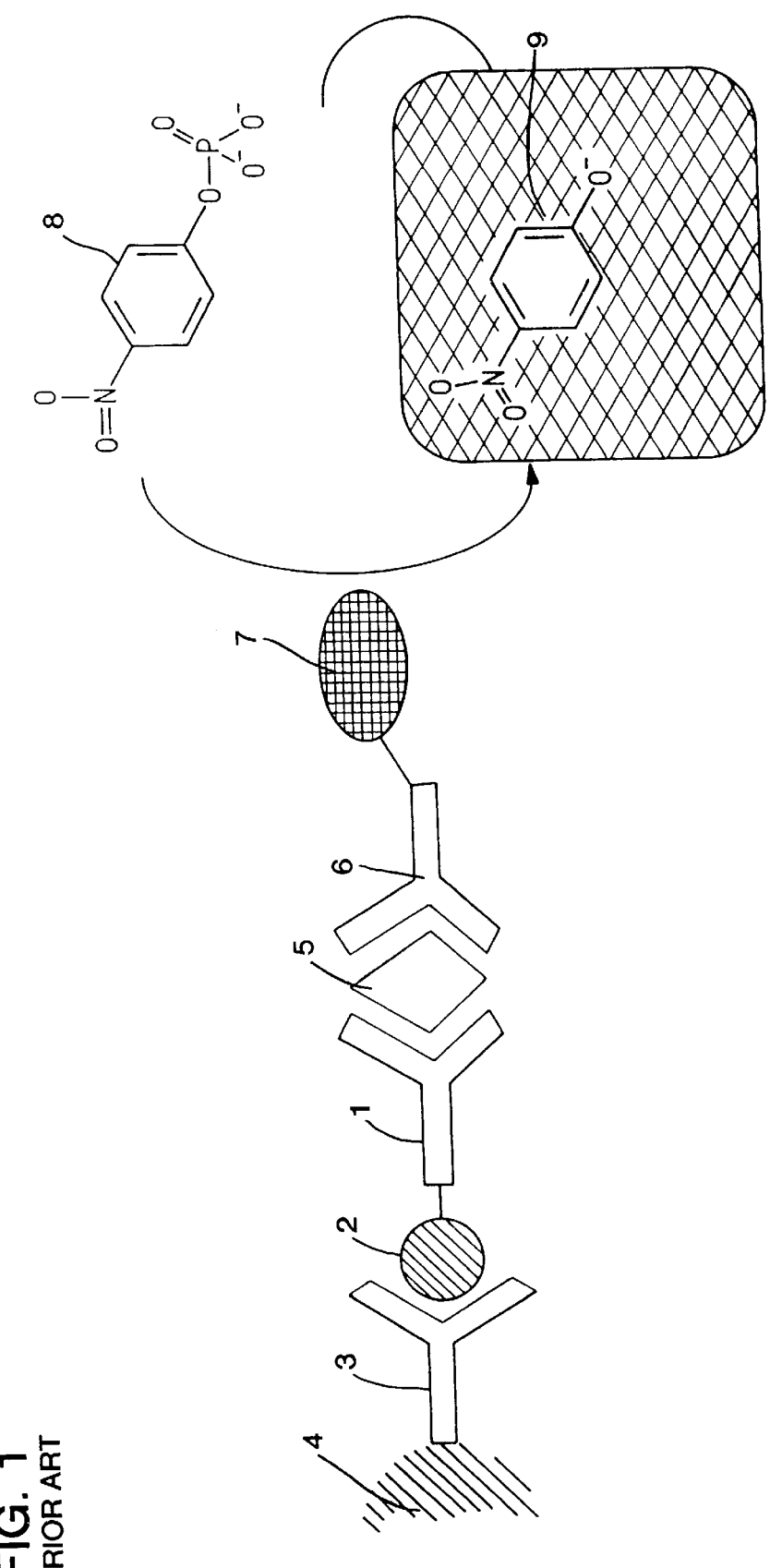
FIG. 1 illustrates a sandwich immunoassay.
Figure 2A:
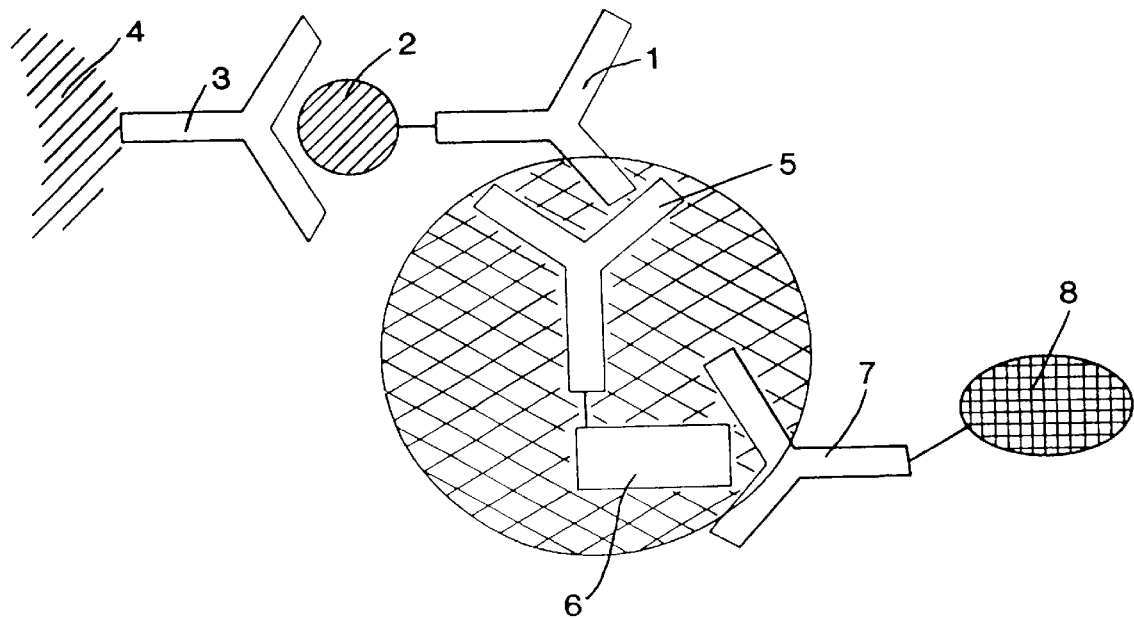
FIG. 2a illustrates a first embodiment of a sandwich immunoassay using a synthetic calibrator according to the present invention.

The present invention relates to a synthetic calibrator which possesses very good stability and which can be used in sandwich immunoassays for determining medically relevant analytes in samples of blood, plasma, serum or urine. The distinctive feature of sandwich immunoassays consists in using two antibodies which are specific for the analyte but which bind to different recognition sites (epitopes) so that the analyte comes to lie between these two antibodies (see FIG. 1). Accordingly, a calibrator for a sandwich immunoassay must also possess two binding sites: one for each of the antibodies employed. Often, the epitope of at least one antibody is known in the form of the amino acid sequence, so that one binding site can consist of this peptide, i.e. of a constituent sequence of the analyte. If the epitope of the second antibody is not known, or if it has a three-dimensional structure, this recognition site cannot be simulated by a peptide. In order to form a sandwich despite this, use can be made of the ability of the antibody to bind to a site other than the antigen recognition site. One possibility consists in employing antibodies, or antibody fragments, which are directed against the said antibody. If this antibody is conjugated to the above mentioned peptide, a synthetic calibrator is obtained which carries a binding site for each of the antibodies used in the sandwich immunoassay (see FIGS. 2a and b).

The chemical conjugation is carried out using known methods which are described in the literature (S. S. Wong, Chemistry of protein conjugation and cross-linking, 1991, CRC Press Inc. ISBN 0-8493-5886-8).

The invention relates, in particular, to a synthetic calibrator material for cardiac troponin I, a heart-specific protein which is of importance in diagnosing acute myocardial infarction. The calibrator consists in each case of a peptide of this analyte, which has been conjugated to antibodies. These antibodies react with the antibodies which are employed in the test for detecting the analyte. The peptides are epitopes of the analyte-specific antibodies, that is, as a rule, protein sequences from the surface of the molecule. They can be prepared using commercially available synthesizers. Peptides are also to be understood as peptide derivatives in which one or more amino acids has been derivatized by means of a chemical reaction. Examples of peptide derivatives according to the invention are, in particular, those molecules in which the backbone and/or reactive amino acid side groups, for example free amino groups, free carboxyl groups and/or free hydroxyl groups, have been derivatized. Specific examples of derivatives of amino groups are sulphonamides or carboxamides, thiourethane derivatives and ammonium salts, for example hydrochlorides. Examples of carboxyl group derivatives are salts, esters and amides. Examples of hydroxyl group derivatives are O-acyl or O-alkyl derivatives.

In addition, the term peptide derivative also encompasses those peptides in which one or more amino acids are replaced by naturally occurring or non-naturally occurring amino acid homologues of the 20 "standard" amino acids. Examples of such homologues are 4-hydroxyproline, 5-hydroxylysine, 3-methylhistidine, homoserine, ornithine, β-alanine and 4-aminobutyric acid. The peptide derivatives must exhibit a specificity and/or affinity of binding to the antibodies which is essentially equivalent to that of the peptides from which they are derived. The length of the peptides is customarily at least 4 amino acids. Preferably, the length is from 4 to 30, and particularly preferably from 4 to 15, amino acids.

A cysteine was attached to the C-terminal end of the peptides in order to facilitate conjugation. For the coupling, a method was selected which was known for protein conjugation (S. Yoshitake et al., Eur. J. Biochem., 101:395, 1979). The antibodies were activated with succinimidyl 4-[N-maleimidamethyl]cyclohexane-1-carboxylate (SMCC), by dissolving 20 mM SMCC in dimethylformamide (DMF) and adding the solution, as a 25-fold excess, to the antibody. The mixture was incubated at 25° C. for 25 min. The reaction was terminated by adding 1 $\mu$M glycine solution (25° C., 10 min). The peptides were bound to the activated antibody either by way of the sulphhydryl group in their sequence or by inserting such a group into them using 2-Iminothiolane (2-IT). The number of peptides per antibody is customarily from 1 to 50, preferably from 1 to 10, and the number of the different peptide sequences is between 1 and 20, preferably 1–5, particularly preferably 1.

Gel chromatography (SUPERDEX 200 (across-linked agarose/dextran matrix)) was carried out in order to purify the calibrator substance, i.e. separate off the low molecular weight peptides. The concentration of the calibrator substance was then determined by UV spectrometry, and the substance was stabilized using 0.5% bovine serum albumin (BSA)/0.1% sodium azide. It is additionally possible to carry out an affinity chromatography purification, using the sequence-specific antibodies which are also employed in the immunoassay, for the purpose of separating off unlabelled antibody.

EXAMPLES

Example 1

A peptide having the sequence RAYATEPHAKKKS (SEQ ID NO: 1) was conjugated to an anti-mouse antibody. The immunoassay was carried out in accordance with the scheme depicted in FIG. 2a. The isotype of the monoclonal antibody was IgG1. Consequently, the anti-mouse calibrator antibody must be directed against IgG1. It does not react with IgG2a (anti-fluorescein, isothiocyanate (anti-FITC) on the magnetic particles. The polyclonal antibody recognizes the peptide having the said sequence. This results in the formation of a sandwich in which the analyte TnI is replaced by the synthetic calibrator.

Automated Sandwich Assay

The artificial calibrator was employed on the automated Immuno 1® Technicon Analyzer (Bayer Diagnostics). The assay format consisted of a sandwich which used the following antibodies: 1. monoclonal antibody against human cardiac troponin I, 2. goat polyclonal antibody which has been affinity-purified against the SEQ ID NO: 1 peptide. The first antibody of the sandwich binds the anti-mouse IgG1 of the artificial calibrator. It is labelled with FITC and is immobilized on magnetic particles by way of anti-FITC. The 2nd antibody of the sandwich reacts with the peptide on the synthetic calibrator. This latter antibody carries alkaline phosphatase and catalyses the colour reaction. The antibodies were incubated sequentially. In this test method, the colour intensity increased in proportion to the concentration of the calibrator substance.

Example 2

Figure 2B:
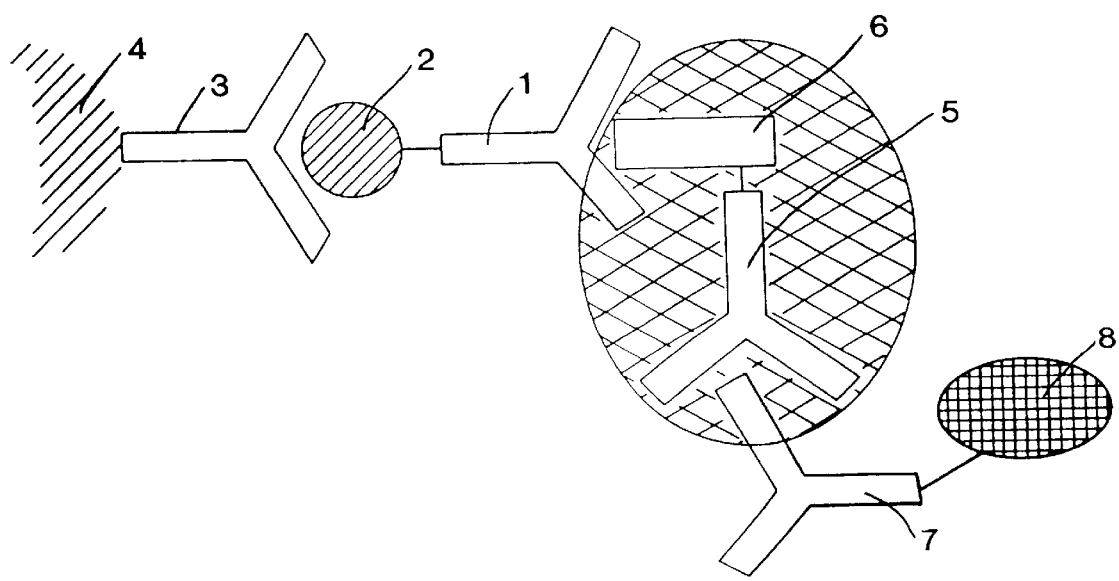
FIG. 2b illustrates a second embodiment of a sandwich immunoassay using a synthetic calibrator according to the present invention.

Another calibrator was formed from the sequence TGLG-FAELQDLCRQIHARVD (SEQ ID NO: 2) and an anti-goat antibody (FIG. 2b). In this case, the monoclonal antibody recognizes the peptide. The anti-goat antibody of the calibrator binds to the goat polyclonal antibody, which latter carries the enzyme for the colour reaction.

Automated Sandwich Assay

The artificial calibrator as described in Example 2 was also employed on the automated Immuno 1® Technicon Analyzer (Bayer Diagnostics). The assay format was a sandwich which used the following antibodies: 1. monoclonal antibody against the SEQ ID NO: 2 of human cardiac troponin I, 2. goat polyclonal antibody against human cardiac troponin. The first antibody of the sandwich binds to the peptide having the SEQ ID NO: 2. This antibody is labelled with FITC and immobilized on magnetic particles by way of anti-FITC. The 2nd antibody of the sandwich reacts with the anti-goat antibody of the synthetic calibrator. It carries alkaline phosphatase and catalyses the colour reaction. The antibodies are incubated sequentially. In this test method, too, the colour intensity increased in proportion to the concentration of the calibrator substance.

---

We claim:

1. A calibrator for use in a sandwich immunoassay for tropinin I, wherein the tropinin I is bound between a first antibody or fragment thereof and a labelled second antibody or fragment thereof said calibrator comprising (a) a third antibody or fragment thereof which specifically binds either (i) to said first antibody or fragment thereof or (ii) to said labelled second antibody or fragment thereof, said third antibody or fragment thereof conjugated to (ii) at least one peptide which consists of an antibody binding site of said troponin I and which specifically binds to whichever of either (i) said first antibody or fragment thereof or (ii) said labelled second antibody or fragment thereof which is not bound by said third antibody or fragment thereof.

2. The calibrator according to claim 1 wherein the at least one peptide has a length of from 4 to 30 amino acids.

3. The calibrator according to claim 1 wherein said third antibody or fragment thereof is conjugated to 1 to 50 peptides, and wherein the peptides consist of 1 to 20 different amino acid sequences of said troponin I.

4. The calibrator according to claim 1 wherein said calibrator is in an aqueous solution.

5. The calibrator according to claim 1 wherein the at least one peptide has an amino acid sequence selected from the group consisting of SEQ ID NO.: 1 and SEQ ID NO.: 2.

6. The calibrator according to claim 1 further comprising one or more auxiliary substances selected from the group consisting of a buffer, a stabilizer, a preservative, a detergent and a cosolvent.

7. In a sandwich immunoassy for determining tropinin I in a sample, wherein the tropinin I in the sample is bound between a first antibody or fragment thereof and a labelled second antibody or fragment thereof to form a complex and the amount of formed complex is measured relative to the amount of complex formed by a known amount of troponin I calibrator to determine the amount of the troponin I in the sample, wherein the improvement comprises using as the calibrator a calibrator comprising (a) a third antibody or fragment thereof which specifically binds either (i) to said first antibody or fragment thereof or (ii) to said labelled second antibody or fragment thereof, said third antibody or fragment thereof conjugated to (ii) at least one peptide which consists of an antibody binding site of said troponin I and which specifically binds to whichever of either (i) said first antibody or fragment thereof or (ii) said labelled second antibody or fragment thereof which is not bound by said third antibody or fragment thereof.

* * * * *